United States Patent [19]
Kaufman

[11] Patent Number: 5,342,349
[45] Date of Patent: Aug. 30, 1994

[54] APPARATUS AND SYSTEM FOR COORDINATING A SURGICAL PLUME EVACUATOR AND POWER GENERATOR

[75] Inventor: David W. Kaufman, Salt Lake City, Utah

[73] Assignee: Sorenson Laboratories, Inc., Salt Lake City, Utah

[21] Appl. No.: 108,396

[22] Filed: Aug. 18, 1993

[51] Int. Cl.⁵ .................. A61M 1/00; A61B 17/36
[52] U.S. Cl. ................................ 606/1; 604/35; 606/34; 606/41
[58] Field of Search ................ 606/1, 34–45; 604/35, 119

[56] References Cited

U.S. PATENT DOCUMENTS

| | | | |
|---|---|---|---|
| 5,041,110 | 8/1991 | Fleenor | 606/37 X |
| 5,167,659 | 12/1992 | Ohtomo et al. | 606/40 |
| 5,180,363 | 1/1993 | Idemoto et al. | 606/39 X |
| 5,211,625 | 5/1993 | Sakurai et al. | 606/39 X |
| 5,242,404 | 9/1993 | Conley et al. | 604/35 X |

*Primary Examiner*—Peter A. Aschbrenner
*Attorney, Agent, or Firm*—Trask, Britt & Rossa

[57] ABSTRACT

A surgical smoke filter and evacuator and a surgical power generator of the type used for electrocautery, laser surgery or the like are combined with an enclosure between the generator and the evacuator. The enclosure directs air which has been filtered of surgical plume contaminants from the evacuator past heat sink elements associated with the generator to facilitate dissipation of heat accumulated incidental to operation of the generator.

12 Claims, 2 Drawing Sheets

APPARATUS AND SYSTEM FOR COORDINATING A SURGICAL PLUME EVACUATOR AND POWER GENERATOR

BACKGROUND OF THE INVENTION

1. The Field

This invention relates to electrosurgery. It is particularly concerned with the filtering and evacuation of surgical plume, and with the cooling of surgical power generator apparatus. It provides an improved structure which provides these functions in a coordinated system.

2. State of the Art

Heretofore, means for evacuating surgical plume have varied widely as to specific features, but generally involve at least a vacuum pressure source and a filtering mechanism. These evacuation means characteristically are autonomous with respect to the source of surgical plume generation.

Among relevant sources of surgical plume generation are laser surgical instruments and electrosurgical devices such as electrocautery styluses with their respective associated power sources. These implements may in some configurations include evacuation ports positioned near the surgical site during surgical procedures to enhance evacuation efficacy. One such device includes upstream vortex creating means to achieve optimal suction reach.

It would be useful to integrate in one coordinated structure a filtered vacuum pressure source with a surgical power generator. Ideally, the principal elements of such a vacuum source/power generator system should be capable of independent operation to afford, for instance, continued surgical function in the event of filter obstruction.

A further benefit would be realized if the system were arranged to exhaust filtered air from the vacuum source through the generator to convectively remove heat produced incidental to operation of the generator. Reduction of heat in this manner could improve cooling efficiency and eliminate the need for cooling components, such as redundant fans and convection fins, considered to be necessary in currently available generators.

SUMMARY OF THE INVENTION

The present invention provides an improved apparatus and system for selectively simultaneously or independently providing power to a surgical appliance which generates surgical plume, and evacuating and filtering such plume from the surgical site with improved efficiency. The system functions to coordinate and enhance the functions of a surgical power generator and surgical plume evacuator. The apparatus thus generally comprises an electrically operable surgical power generator, a surgical plume evacuator and structural means for either attaching the generator and the evacuator together or combining them into a single device.

In one embodiment of the present invention, the generator may provide power for electrosurgical applications, laser applications or other such heat-producing and surgical plume-generating procedures. The generator includes an encasement defining the interior of the generator; fluid communication means, such as one or more air ducts formed in a wall, preferably the base plate, of the encasement to allow fluid communication with the interior of the generator; heat dissipation means, such as a heat sink structure, for transfer of heat generated by the generator away from the generator; and heat vents formed in the encasement proximal the heat sink structure. The heat sink structure may incorporate structural means, such as convection fins, to enhance the amount and rate of lateral or other convective dissipation of the heat away the heat sink structure.

The surgical plume evacuator generally includes a prime mover, such as an electric motor; evacuation means, such as a vacuum pump driven by the motor; a surgical plume filter and a housing which defines an interior space and an exterior space. The vacuum pump typically includes a negative pressure port and a positive pressure port. The surgical plume filter is typically constructed and arranged with a distal opening in fluid communication with the negative pressure port of the vacuum pump, and has a proximal opening through which surgical plume may be drawn. The proximal opening of the filter is located outside of the housing, in the exterior space, and the positive pressure port is located inside of the housing, in the interior space.

The present invention also may incorporate attachment means for securing the generator and the evacuator together. In such an arrangement, the housing and the base of the generator are in substantially fluid-tight relation, except for the fluid communication means and the positive pressure port. The housing and the generator base then define the interior space.

A significant benefit of the system of this invention is that the vacuum pump generates negative pressure at the proximal opening of the filter and thereby draws surgical plume away from a surgical site, through the filter and out of the positive pressure port into the interior space of the housing. Upon introduction of additional filtered air into the otherwise substantially fluid-tight interior space, the filtered air is forced to continue through the fluid communication means, (most often air ducts,) past the heat sink structure, and eventually to the exterior space through heat vents. Excess heat is thereby carried by convection with the displaced filtered air away from the heat sink structure and thus away from the generator.

In another embodiment, an apparatus combines a surgical power generator and a surgical plume evacuation means substantially within a shell. The shell thus defines an interior space and an exterior space, with the apparatus positioned within the interior space. The shell incorporates heat vents formed through the shell. The heat vents provide fluid communication between the interior and exterior spaces.

Accordingly, upon operation of the apparatus, air contaminated with impurities is evacuated from the surgical site in the form of surgical plume into and through the filter. Filtered air continues from the distal opening of the filter through the negative pressure port and the vacuum pump, out the positive pressure port and into the interior space within the shell of the apparatus. As pressure within the interior space thus increases, the filtered air is displaced through the heat vents and past the heat sink means to the exterior space, thereby dramatically enhancing the convective dissipation of the heat incidentally generated by operation of the surgical generator.

The system of this invention is useful with any surgical generator, the operation of which results in the incidental generation of heat and surgical plume. The generator may be in the form of an electrosurgical power generator or a laser surgical power generator, for example.

Significantly, combination of the generator and evacuation in functionally substantially fluid-tight relation with respect to each other, obviates the need for a fan within a surgical power generator to blow air past heat sink elements and out heat vents for convective dissipation of incidental heat.

Similarly, the surface area required to provide adequate cooling by convection fins or the like dramatically reduced. A significant benefit of this reduction is a concomitant reduction in the amount of conductive materials needed to provide such surface area.

The apparatus of this invention may be embodied to permit the surgical power generators and surgical plume filtering and evacuation subsystems to function concurrently or autonomously. Should a filter becomes clogged with impurities, for example, the surgery in process may continue while the filter is replaced.

BRIEF DESCRIPTION OF THE DRAWINGS

In the drawings, which illustrate what is currently regarded as the best mode for carrying out the invention.

DETAILED DESCRIPTION OF THE ILLUSTRATED EMBODIMENTS

It will be readily understood that the components of the present invention, as generally described and illustrated in the Figures, could be arranged and designed in a wide variety of different configurations. Thus, the following detailed description of the illustrated embodiments is not intended to limit the scope of the invention, as claimed, but it is merely representative of the presently preferred embodiments of the invention.

Figure 1:
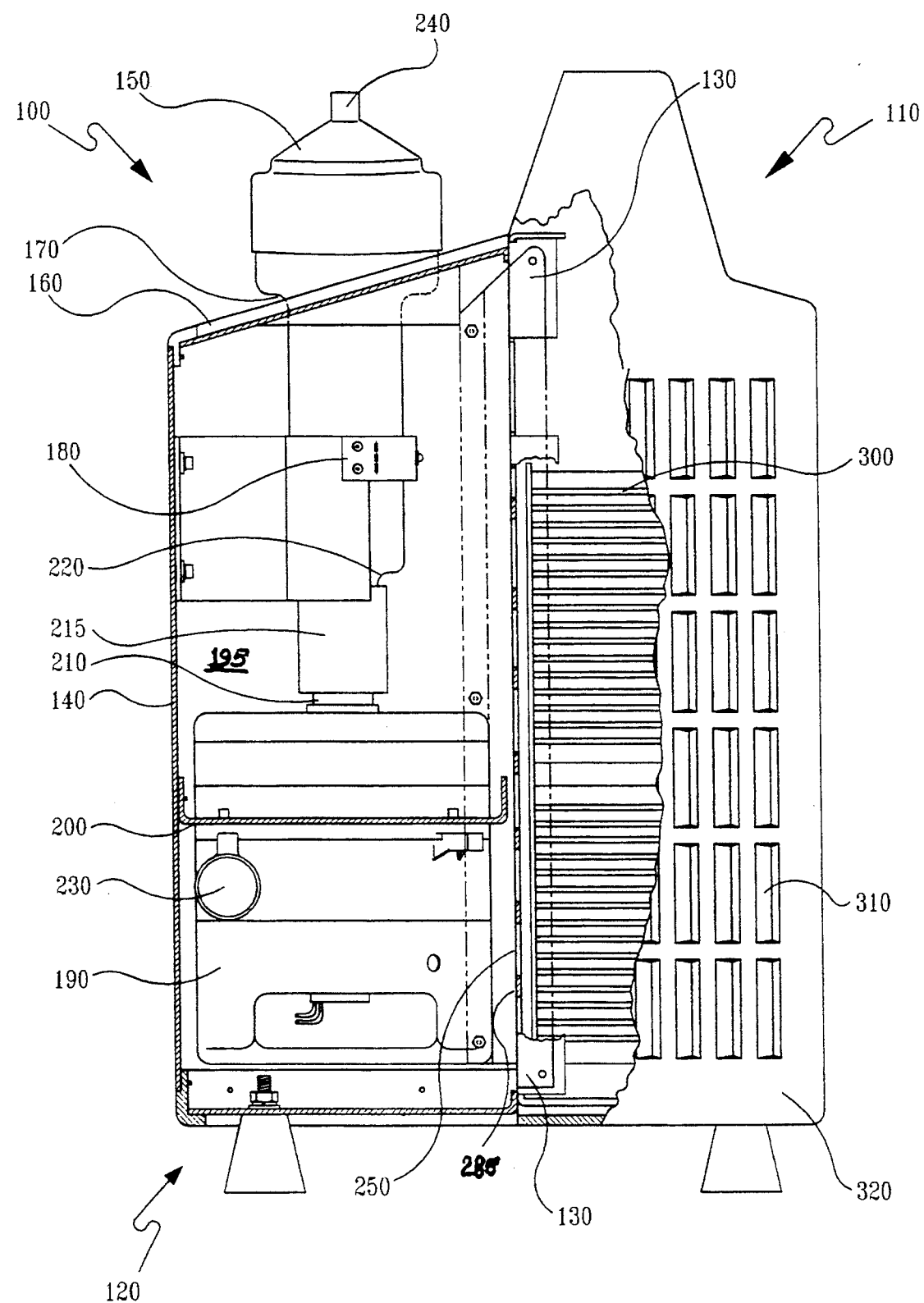
FIG. 1 is a partially cut away cross-sectional lateral view of a preferred embodiment of the assembled invention.

Referring particularly to FIG. 1, a presently preferred embodiment of the device, designated generally 100, includes a solid state electrosurgical generator, designated generally 110. A suitable such generator is currently available from Pfizer, Inc. under the trademarks "Valleylab®" and "Force 2 ™." The generator 110 and an evacuation assembly, designated generally 120, are connected to each other by an adaptor plate 130 (illustrated in fantom lines in FIG. 1,) which is bolted along its length to both the generator 110 and the housing 140 of the assembly 120.

The housing 140 of the evacuation assembly 120 partially encases a filter capsule 150 located during use at the front wall 160 of the device 100. The capsule 150 is removably inserted through a filter window 170 formed in the front wall 160 of the housing 140, and when seated within the housing 140 is anchored within a filter bay 180. An electrically operable vacuum pressure generating motor 190, held in place by a motor frame 200, is completely encased within the housing 140, and is seated immediately behind the filter capsule 150.

The negative pressure port 210 of the vacuum motor 190 is in fluid communication with a coupler 215, which couples the negative pressure port 210 with the distal (rear) opening 220 of the filter capsule 150. The positive pressure port 230 of the motor 190 is in fluid communication with the interior space 195 within the housing 140. Suctioned air is drawn from the proximal (front) opening 240 of the filter capsule 150 through the filter capsule 150 and the motor 190 and exhausted from the motor 190 directly into the housing space 195.

Figure 2:
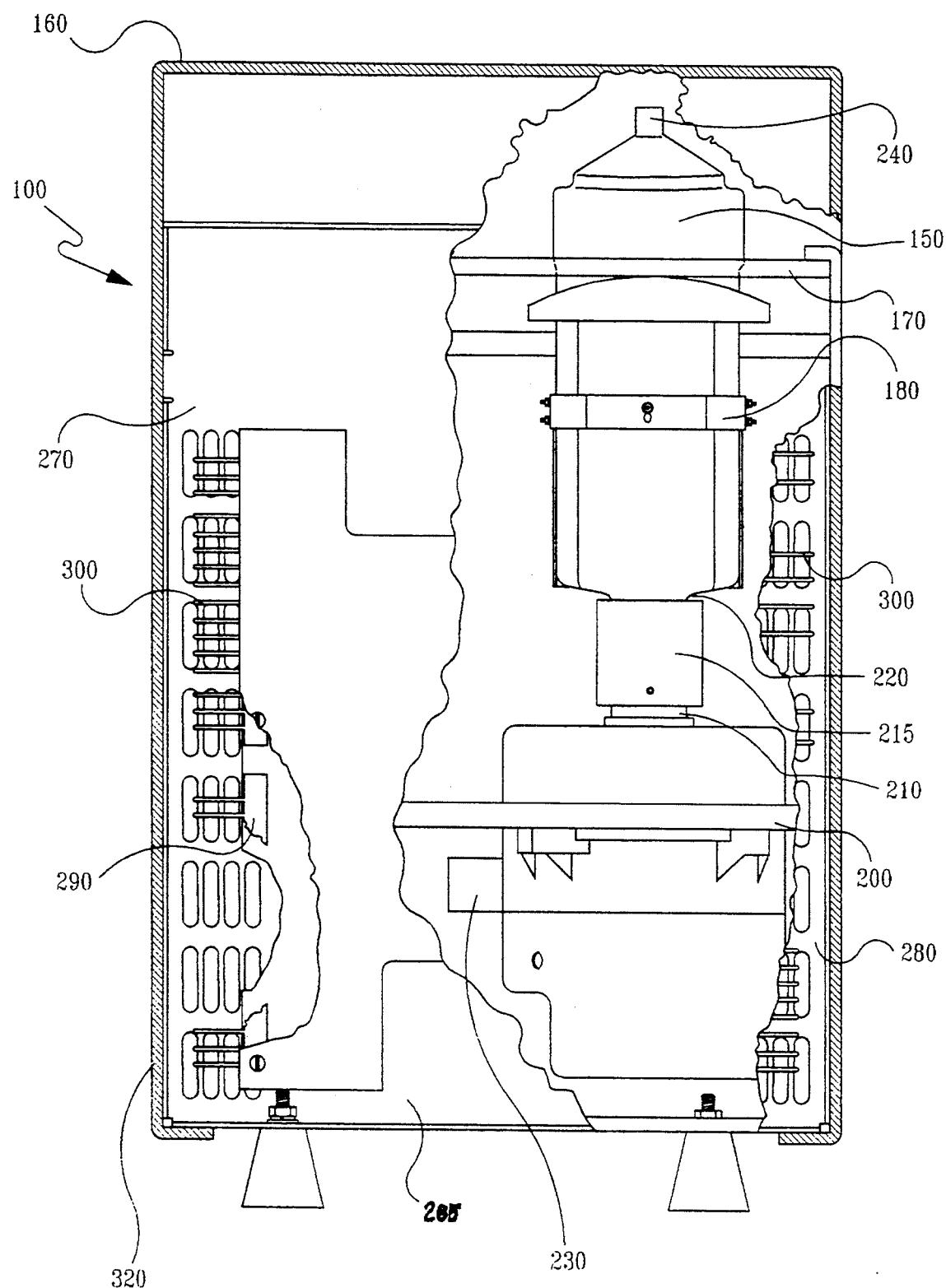
FIG. 2 is a partially cut away cross-sectional top view of an alternative embodiment.

With no alternative path of flow, the air thus exhausted into the housing 140 escapes through air ducts 250 positioned along a first side 270 and a second side 280 of the base plate 285, as is most clearly illustrated in FIG. 2. After passing beyond these air ducts 250, the air is further positively displaced in the same direction past sink elements 290, which are structurally and functionally associated with the generator 110. The air thus travels between convection fins 300 extending from each heat sink element 290, and is finally exhausted outside of the device 100 through heat vents 310, which open in the encasement 320 of the generator 110 adjacent the heat sink elements 290.

Reference in this disclosure to specific details of the illustrated embodiment is not intended to restrict the scope of the appended claims, which themselves recite those features regarded as important to the invention.

What is claimed is:

1. A system, comprising:
   an electrically operable surgical power generator including:
   (a) an encasement defining the interior of said generator;
   (b) fluid communication means formed in a base of said encasement for communicating fluid to said interior;
   (c) heat sink structure for transfer of heat generated by said generator away from said generator; and
   (d) heat vents formed in said encasement proximal said heat sink structure;
   a surgical plume evacuator including:
   (a) an electrically operable motor;
   (b) vacuum pump means driven by said motor and having a negative pressure port and a positive pressure port;
   (c) a surgical plume filter having a distal opening in fluid communication with said negative pressure port and having a proximal opening; and
   (d) a housing defining a space outside of which said proximal opening is located and inside of which said positive pressure port is located; and
   attachment means for securing said generator and said evacuator together, whereby said space and said base are in substantially fluid-tight relation except for said fluid communication means and said positive pressure port.

2. The system of claim 1, wherein said heat sink structure comprises convection means for lateral dissipation of heat generated by said generator.

3. The system of claim 1, wherein said electrically operable surgical power generator comprises an electrosurgical power generator.

4. The system of claim 3, wherein said heat sink structure comprises convection means for lateral dissipation of heat generated by said generator.

5. The system of claim 1, wherein said electrically operable surgical power generator comprises a laser surgical power generator.

6. The system of claim 1, wherein said fluid communication means comprise at least one air duct formed in a base of said encasement.

7. An apparatus, comprising:
   a surgical power generator, including heat sink means for transfer of heat generated by said generator away from said generator;

surgical plume evacuation means, including a motor, a vacuum pump means driven by said motor, said pump having a negative pressure port and a positive pressure port, and a filter, having a distal opening in fluid communication with said negative pressure port and having a proximal opening; and a shell, defining an interior space and an exterior space; said shell including heat vents formed through said shell and positioned proximal said heat sink means, said proximal opening being located in the exterior space and said positive pressure port being located in said interior space.

8. The apparatus of claim 7, wherein said heat sink means comprises convection means for lateral dissipation of heat generated by said generator.

9. The apparatus of claim 7, wherein said generator comprises an electrosurgical power generator.

10. The apparatus of claim 9, wherein said heat sink means comprises convection means for lateral dissipation of heat generated by said generator.

11. The apparatus of claim 7, wherein said generator comprises a laser surgical power generator.

12. The apparatus of claim 7, wherein said interior space is substantially in fluid tight relation with respect to exterior space, except for said positive pressure port and said heat vents.

* * * * *